US00PP22943P2

(12) United States Plant Patent
Probst

(10) Patent No.: US PP22,943 P2
(45) Date of Patent: Aug. 7, 2012

(54) ***COREOPSIS* PLANT NAMED 'COSMIC EVOLUTION'**

(50) Latin Name: ***Coreopsis* hybrid**
Varietal Denomination: Cosmic Evolution

(76) Inventor: Darrell R. Probst, Hubbardston, MA (US)

( * ) Notice: Subject to any disclaimer, the term of this patent is extended or adjusted under 35 U.S.C. 154(b) by 21 days.

(21) Appl. No.: 12/932,911

(22) Filed: Mar. 9, 2011

(51) Int. Cl.
*A01H 5/00* (2006.01)

(52) U.S. Cl. ..... Plt./417

(58) Field of Classification Search ..... Plt./417
See application file for complete search history.

*Primary Examiner* — Susan McCormick Ewoldt
(74) *Attorney, Agent, or Firm* — Penny J. Aguirre

(57) ABSTRACT

A new cultivar of hybrid *Coreopsis* named 'Cosmic Evolution' characterized by its large inflorescences with ray florets that are creamy white in color and becoming suffused with red-purple as temperatures cool with the purple coloration beginning as an eyezone and on the margins of the petals and then progressing until the flowers become nearly solid red-purple, its ability to bloom from June until frost in Massachusetts, its vigorous growth habit and healthy foliage, and its reliably perennial habit and cold hardiness at least to U.S.D.A. Zone 4.

2 Drawing Sheets

Botanical classification: *Coreopsis* hybrid.
Variety denomination: 'Cosmic Evolution'.

CROSS REFERENCE TO A RELATED APPLICATION

This application is co-pending with a U.S. Plant Patent Applications filed for plants derived from the same breeding program that is entitled *Coreopsis* Plant Named 'Star Cluster' (U. S. Plant patent application Ser. No. 12/932,910 pending), *Coreopsis* Plant Named 'Cosmic Eye' (U.S. Plant Pat. No. 22,601), and *Coreopsis* Plant Named 'Galaxy' (U.S. Plant Pat. No. 21,999), *Coreopsis* Plant Named 'Redshift' (U.S. Plant Pat. No. 20,412) and *Coreopsis* Plant Named 'Full Moon' (U.S. Plant Pat. No. 19,364).*

BACKGROUND OF THE INVENTION

The present invention relates to a new and distinct cultivar of *Coreopsis* plant, botanically of hybrid origin and known as *Coreopsis* 'Cosmic Evolution' and will be referred to hereinafter by its cultivar name, 'Cosmic Evolution'. The new cultivar of *Coreopsis* is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A Zone 5 in a wide range of flower colors and plant forms. The inventor collected seed in the wild from five different species that are not commercialized and made six generations of crosses to produced interspecific hybrids to utilize in his breeding work.

The Inventor made a controlled cross in the summer of 2007 in his test garden in Hubbardston, Mass. between an unnamed sibling of *Coreopsis* 'Redshift' as the female parent and an unnamed F1 *Coreopsis rosea*×complex hybrid as the male parent. 'Cosmic Evolution' was selected September of 2008 as a single unique plant amongst the resulting seedlings.

Asexual reproduction of the new cultivar was first accomplished by stem cuttings under the direction of the Inventor in Kensington, Conn. in September 2008. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Cosmic Evolution' as unique from all *Coreopsis* cultivars and species known to the Inventor.

1. 'Cosmic Evolution' exhibits inflorescences with ray florets that are creamy white in color (base color) in the summer heat and become suffused with red-purple as temperatures become cool. In cooler temperatures, the red-purple coloration begins as an eyezone and on the margins of the petals and then progresses until the flowers become nearly solid red-purple.
2. 'Cosmic Evolution' exhibits large inflorescences (up to 7.6 cm (3 inches) in diameter).
3. 'Cosmic Evolution' blooms from June until frost in Massachusetts.
4. 'Cosmic Evolution' exhibits a vigorous growth habit with healthy foliage.
5. 'Cosmic Evolution' exhibits a reliably perennial habit and is cold hardy at least to U.S.D.A. Zone 4.

The female parent differs from 'Cosmic Evolution' in having smaller inflorescences that have a yellow base color. The male parent differs from 'Cosmic Evolution' in having smaller inflorescences that are solid pale yellow in color throughout the season. 'Cosmic Evolution' can be compared to *Coreopsis* cultivars 'Redshift' (U.S. Plant Pat. No. 20,412) and 'Snowberry' (U.S. Plant Pat. No. 18,560). 'Redshift' differs from 'Cosmic Evolution' in having smaller inflorescences that are light yellow in color and suffused with red in cool temperatures rather than purple. 'Snowberry' differs from 'Cosmic Evolution' in having much smaller inflorescences that have a light yellow base color.

BRIEF DESCRIPTION OF THE DRAWING

The accompanying colored photographs illustrate the overall appearance and distinct characteristics of the new *Coreopsis*. The photographs were taken of a one year-old plant of 'Cosmic Evolution' grown in a one-gallon container in Hubbardston, Mass.

The photograph in FIG. 1 shows a top view of 'Cosmic Evolution' in bloom.

Figure 2:
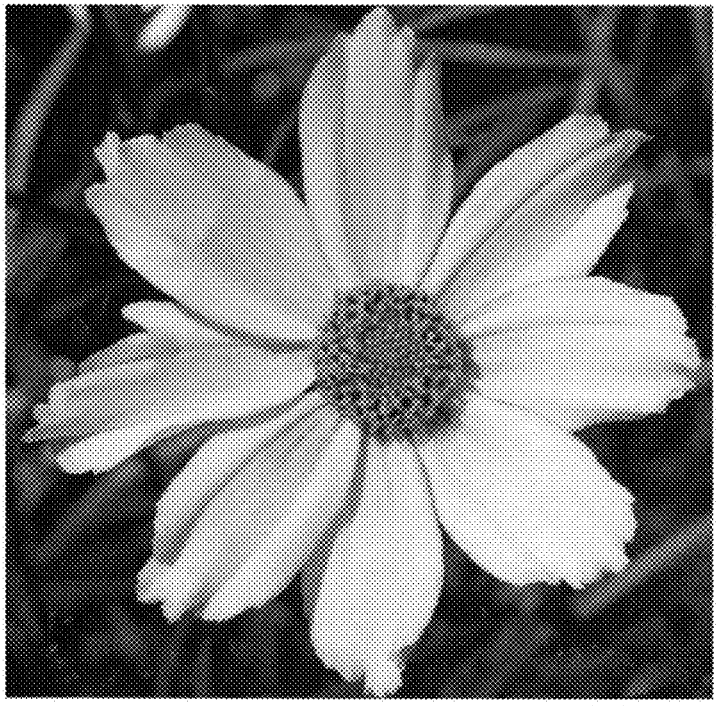
Figure 3:
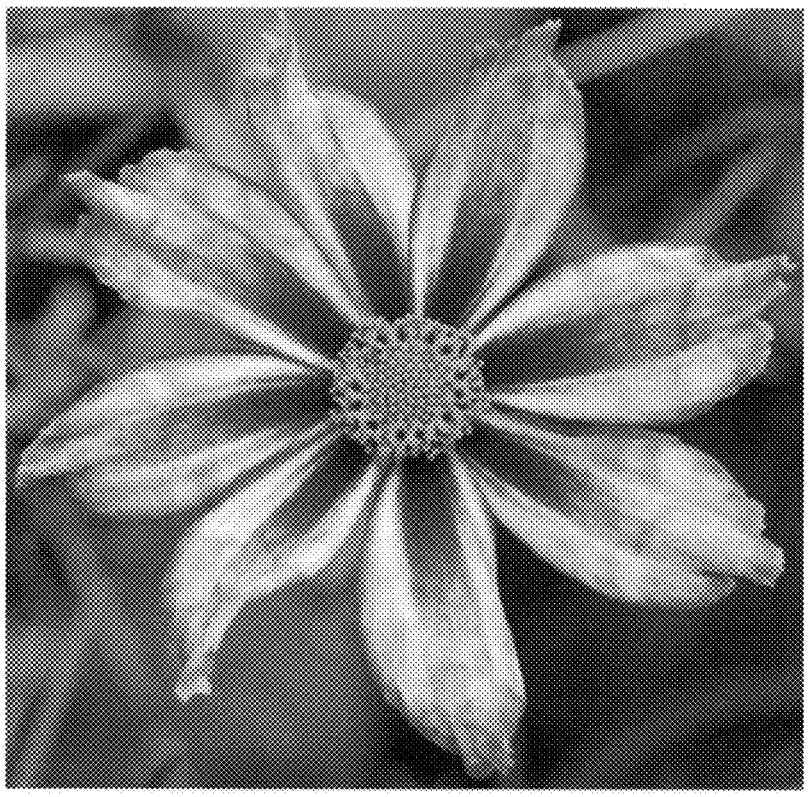
Figure 4:
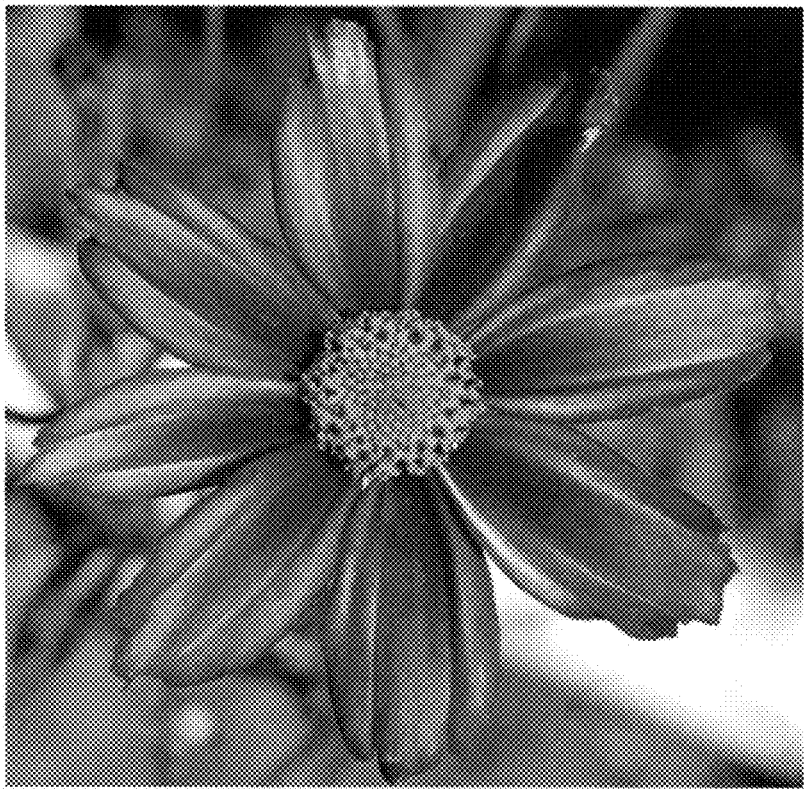

The photograph in FIG. 2, FIG. 3, and FIG. 4 provide close-up views of inflorescences of 'Cosmic Evolution'.

Figure 1:
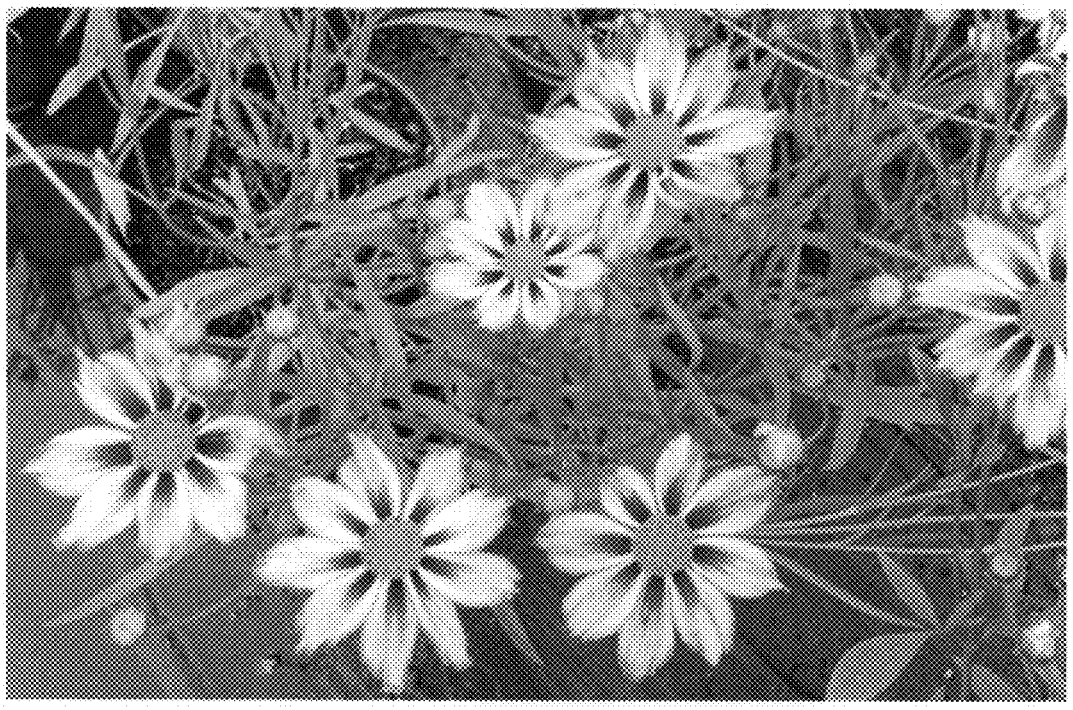

FIG. 1 was taken in summer, FIG. 2 was taken in fall as nights began to cool, and FIG. 4 was taken in fall just before frost. The colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for two years in a trail garden in Hubbardston, Mass. with the detailed botanical data collected from six month-old plants of the new cultivar as grown in one-gallon containers in Kensington, Conn. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period*.—Blooms from June until frost in central Massachusetts.

*Plant habit*.—Herbaceous perennial, clump-forming, compact, canopy upright and spreading.

*Height and spread*.—Reaches 45 to 60 cm (18 to 24 inches in height) and spread after 3 months from a cutting.

*Cold hardiness*.—At least to U.S.D.A Zone 4.

*Diseases resistance*.—No particular resistance or susceptibility to diseases was observed.

*Root description*.—Fibrous, fine and well-branched.

Growth and propagation:

*Propagation*.—Terminal stem cuttings and division.

*Growth rate*.—Vigorous.

Stem description:

*Shape*.—Rounded, solid.

*Stem color*.—144B.

*Stem size*.—Main stem an average of 30 cm in length and 3 mm in width with laterals variable in length and an average of 8 cm in length (excluding peduncles) and 2 mm in width.

*Stem surface*.—Glabrous.

*Branching habit*.—An average of 12 basal branches, each with 3 to 4 secondary branches, arising opposite at nodes, branch internode is variable but typically about 5 cm.

Foliage description:

*Leaf division*.—Simple.

*Leaf margins*.—Entire, ciliate towards base, cilia about 1 mm in length, 155C in color.

*Leaf size*.—Variable, an average of 6 cm in and 3 mm in width.

*Leaf shape*.—Linear.

*Leaf base*.—Cuneate.

*Leaf apex*.—Narrowly acute.

*Leaf venation*.—Pinnate, not prominent, coloration same as leaf on both surfaces 138B.

*Leaf attachment*.—Sessile.

*Leaf arrangement*.—Opposite.

*Leaf surface*.—Dull, glabrous.

*Leaf color*.—Young and mature upper surface; 138B, young and mature lower surface; 138B.

Flower description:

*Inflorescence type*.—Composite with double ray florets surrounding disk florets in the center, forming a radiant head, inflorescences are borne on branch terminals.

*Lastingness of inflorescence*.—About one week until senescence of ray flowers, bracts and disk flowers are persistent.

*Fragrance*.—None detected.

*Quantity of inflorescences*.—1 per lateral branch, an average of 20 per plant grown in a one-gallon container.

*Inflorescence size*.—An average of 1.7 cm in depth and 6.5 cm in diameter with disk portion an average of 1 cm in diameter.

*Inflorescence buds*.—Average of 4 mm in depth and 8 mm in diameter, shape is flattened spherical, 138D in color surrounded by 8 bracts 138B in color.

*Peduncle*.—Strong, an average of 10 cm in length and 1.7 mm in diameter, 138A in color, glabrous surface.

Involucral bracts:

*Bract number*.—Two rows of 8.

*Bract arrangement*.—Outer bracts are un-fused and reflexed when flower is fully open and becoming horizontal after ray florets drop, inner bracts overlap and surround receptacle with a campanulate form with apical portion un-fused, spreading, and held close to lower surface of ray florets.

*Bract size*.—Outer bracts; up to 1 cm in length and 2 mm in width, inner bracts; up to 1.4 cm in length and 4 mm in width with free portion an average of 7 mm in length and 4 mm in width.

*Bract color*.—Outer bracts; 138B in both surfaces, inner bracts; 145A with apex and margin N144A.

*Bract texture*.—Glabrous on outer and inner bracts.

*Bract apex*.—Acute on outer and inner bracts.

*Bract base*.—Truncate on inner and outer bracts.

*Bract margins*.—Entire.

*Bract shape*.—Outer bracts; linear, inner bracts; broadly lanceolate.

Ray florets (sterile):

*Number*.—An average of 8 arranged primarily in two alternating rows.

*Size*.—An average of 2.7 cm in length and 1.3 cm in width.

*Apex*.—3-noticed with center lobe emarginate and side lobes acute.

*Base*.—Broadly cuneate.

*Margins*.—Entire on sides, notched at apex.

*Aspect*.—Held primarily horizontal.

*Texture*.—Glabrous on upper and lower surfaces.

*Color*.—Upper and lower surface when opening and mature in summer; NN155A, in fall and in cool temperatures; NN155A with base section (eyezone) 183C and margins 183C on sides and N77C on the apex, and as they mature can become almost completely suffused with 183C, N77C and a blending of the two colors.

Disk flowers (perfect):

*Shape*.—Tubular, corolla is fused, flared at apex.

*Number*.—About 200.

*Size*.—About 7 mm in length and 1 mm in width.

*Color*.—En masse; 20A when fully open and becoming 163B when mature, corolla; base (tube) is 1C in color, flared portion is 20A and translucent.

*Receptacle*.—About 8 mm in diameter and 4 mm in depth, N144C in color.

Reproductive organs:

*Presence*.—Disk flowers are perfect, ray flowers are sterile.

*Gynoecium*.—1 Pistil, 5 mm in length, style is very fine and about 1C in color and translucent, bifid pilose stigma is 20A in color with branches about 1 mm in length and recurved, ovary is 1.5 mm in length, 1 mm in width, inferior, and 147C in color.

*Androcoecium*.—5 stamens, fused into tube surrounding style, 2 mm in length and 0.7 mm in width, about 165A in color, no pollen was observed.

*Fruit/seed*.—No fruit or seed development was observed.

It is claimed:

1. A new and distinct cultivar of *Coreopsis* plant named 'Cosmic Evolution' as herein illustrated and described.

* * * * *